United States Patent [19]

Doody

[11] Patent Number: 5,514,598
[45] Date of Patent: May 7, 1996

[54] PRENATAL DETECTION OF MECONIUM

[76] Inventor: Michael Doody, 4203 Towanda Trail, Knoxville, Tenn. 37919

[21] Appl. No.: 159,794

[22] Filed: Nov. 30, 1993

[51] Int. Cl.⁶ .................. G01N 33/53; G01N 33/543; C07K 16/18; C07K 17/02
[52] U.S. Cl. .................. 436/518; 436/530; 436/535; 435/7.1; 435/7.9; 435/7.92; 435/7.94; 530/387.1; 530/391.1; 530/412; 530/417
[58] Field of Search .................. 435/7.9, 7.1, 7.92, 435/7.94; 436/518, 535, 530; 530/412, 417, 387.1, 391.1

[56]   References Cited

U.S. PATENT DOCUMENTS

| | | | |
|---|---|---|---|
| 4,818,709 | 4/1989 | Primus et al. | 436/518 |
| 5,009,507 | 4/1991 | Katz | 356/421 |
| 5,015,589 | 5/1991 | Ostrea, Jr. | 436/92 |
| 5,172,693 | 12/1992 | Doody | 128/633 |
| 5,185,267 | 2/1993 | Ostrea, Jr. | 436/92 |
| 5,223,440 | 6/1993 | Teng et al. | 436/510 |

OTHER PUBLICATIONS

Goldenberg, D. M., et al. "Carcinoembryonic Antigen Present in Meconium: The Basics of a Possible New Diagnostic Test of Fetal Distress." American Journal of Obstetrics and Gynecology 113(1): 66–69, 1972.

Francoual, J., et al. "Corporphyrin in Urine of Newborns with Meconium Aspiration Syndrome," Clinical Chemistry 29(12): 2054–2056, 1983.

Harlow, E. & Lane, D. Antibodies: A Laboratory Manual—Cold Spring Harbor, NY: Cold Spring Harbory Laboratory, 1988. Pp. 61, 473–510.

Kobayashi, H., et al. "A Sample, Noninvasive Method for Diagnosis of Amniotic Fluid Embolism by Monoclonal Antibody TKH–2 that Recognizes Neu Ac∝2-6 GalNAc" American J. Obstetrics & Gynecology 3(1) 849–853, Mar., 1993.

Seppälä, Markku et al. "Radioimmunoassay of Oxytocin in Amniotic Fluid, Fetal Urine, and Meconium during Late Pregnancy and Delivery." Am. J. Obstet. Gynecol. 114(6) 788–791, 1972.

Wisdom, G. B. "Enzyme Immunoassay" Clin. Chem. 22(8): 1243–1255, 1976.

Vick, R. L. Contemporary Medical Physiology. Menlo Park, CA: Addison–Wesley, 1984. Pp. 875–876.

Jalanko, H. et al. J. Clin. Pathol. 38: 1065–1072, 1985.

Primus, F. J. et al. Immunological Heterogeneity of Caraneembryonic Antigen . . . Cancer Research 43: 679–685, 1983.

*Primary Examiner*—Toni R. Scheiner
*Assistant Examiner*—Eve L. Wilson
*Attorney, Agent, or Firm*—Pravel, Hewitt, Kimball & Krieger

[57]   ABSTRACT

Meconium State Pregnancy is diagnosed by analysis of prenatal maternal fluids for the presence of specific meconium antigens, including a specific meconium protein antigen of approximately 14 KD.

10 Claims, 1 Drawing Sheet

PRENATAL DETECTION OF MECONIUM

FIELD OF THE INVENTION

This invention relates to non-invasive prenatal diagnosis of meconium state pregnancy, and more particularly to a method for the detection of a meconium antigen in prenatal maternal fluids, including urine.

BACKGROUND OF THE INVENTION

Meconium, a term referring collectively to mucus, bile, epithelial cells, and other products, accumulates in the fetal colon. Meconium is normally excreted within one or two days after birth, however, stress during pregnancy can cause the fetus to expel meconium into the surrounding amniotic fluid. The presence of meconium in the amniotic fluid, "Meconium State Pregnancy," is indicative of a need for more intensive early labor monitoring.

Infants born with meconium in their amniotic fluid have lower overall infant assessment scores than their peers born without meconium in the amniotic fluid. Another danger associated with the presence of meconium is the risk of the infant aspirating meconium into its lungs at the time of birth. Meconium Aspiration Syndrome is a very severe form of pneumonia that is a life-threatening problem for approximately ten to twenty infants per ten thousand born. Meconium Aspiration Syndrome is also a significant cause of cerebral palsy. Because of these and other risks correlated with Meconium State Pregnancy, infants born with meconium in the amniotic fluid (meconium staining) have higher mortality and morbidity rates than infants without meconium staining. A method permitting early prenatal detection of meconium excretion by the fetus would be highly desirable.

Currently, the presence of meconium in the amniotic fluid can be diagnosed only by visualization of dark staining pigments in the amniotic fluid. Meconium staining may be directly visualized by inspection of amniotic fluid at the time of placental membrane rupture, but such late detection is generally not of any practical value. Meconium may be visually detected in amniotic fluid obtained during amniocentesis. This invasive procedure is not performed for all pregnancies, and is too severe a procedure to be considered for routine, e.g. monthly, monitoring of meconium. In addition, amniotic fluid which looks relatively clear by visual inspection may contain significant amounts of meconium.

Recently, a probe has been described which utilizes illumination of the amnion with light of a specific wavelength. The probe detects fluorescence of biological pigments contained within meconium (U.S. Pat. No. 5,172,693). While this procedure permits prenatal detection of meconium, a more specific procedure which does not rely on visual inspection and which may detect smaller amounts of meconium as well as non-colored meconium would be highly desirable.

SUMMARY OF THE INVENTION

Figure 1:
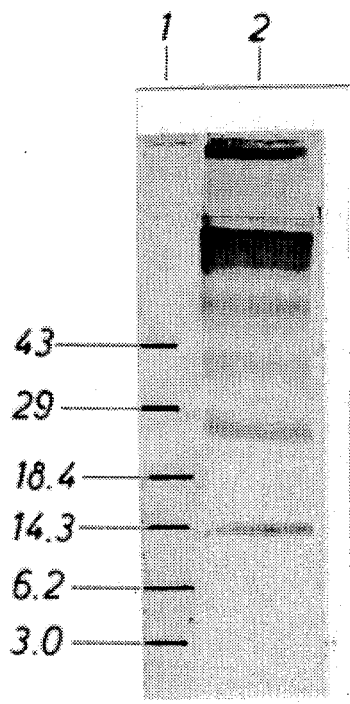
FIG. 1 is a photograph of a polyacrylamide gel stained with Commassie blue: Lane 1 contains molecular weight standards; lane 2 contains control meconium.

The present invention includes a specific, simple, and non-invasive method for the detection of meconium in prenatal fluids, including urine. Specific meconium antigens including a protein antigen of approximately 14K molecular weight (14 KD), have been identified in maternal fluids which are characteristic of Meconium State Pregnancy and diagnostic of the presence of meconium in the amniotic fluid. Specific anti-meconium antibodies bind meconium antigens in complex prenatal fluids including serum and urine as well as in amniotic fluid which may not be visually "stained." Routine diagnostic methods including polyacrylamide gel electrophoresis, ELISA, immunoblots, and the like are used to detect and quantify meconium antigens in prenatal sample fluids. Such methods permit early detection of very small amounts of meconium which may not be detected by visual inspection of amniotic fluids.

By the method of the claimed invention, a pregnancy may be monitored, for example by analysis of prenatal urine samples, to permit early detection of meconium and early diagnosis of potentially problematic pregnancies.

DETAILED DESCRIPTION OF THE PREFERRED EMBODIMENT

In the method of the present invention, prenatal maternal fluids including urine, blood, and amniotic fluid are monitored for the presence of meconium antigens. The presence of meconium antigens in prenatal maternal fluids is diagnostic of meconium excretion by the fetus and of Meconium State Pregnancy. As defined herein, a meconium antigen is a compound normally present in meconium, which compound can be specifically detected when present in amniotic fluid, urine, or blood.

Meconium antigens present in prenatal fluids are detected, for example, by analysis of prenatal fluid samples by chromatography, e.g., gel electrophoresis, one or two dimensional, and comparison of protein patterns obtained from prenatal samples with protein patterns of known meconium antigens. For example, a unique meconium protein antigen of approximately 14 kilodaltons (KD) is present in the urine of pregnant women who show meconium stained amniotic fluid at parturition. The presence of this antigen in a test sample is diagnostic of Meconium State Pregnancy.

In a preferred embodiment, meconium antigens are detected by immunological methods, i.e., by binding to an anti-meconium antibody. Anti-meconium antibodies may be adapted for use in various ELISA or Western blot analyses, for example, which may be used in a diagnostic "kit" form for ready use in a physician's office or for at home use.

In a most preferred embodiment, meconium antigens present in a test sample are captured onto a solid substrate, for example, by an anti-meconium antibody, or by a non-selective binding mechanism such as nitrocellulose paper or plastic test wells. Captured meconium antigen is then detected and quantified, for example, by antibody binding and/or visualization with marker systems known in the field, e.g., labeled antibody techniques, double antibody techniques, and the like.

Antibodies to meconium are produced by polyclonal or monoclonal methods known to those of skill in the art. Total or fractionated meconium is administered alone, or in combination with an adjuvant to animals, e.g., rabbits, sheep, horses, for the production of antibodies. Resultant antis era is then screened for anti-meconium activity, for example, the ability to selectively bind meconium antigens in the presence of complex fluids such as urine and serum, for example by radio immunoassay, enzyme linked immunoassay (ELISA) or Western blot analysis.

The inventive method has surprisingly identified meconium antigens which cross the amniotic membranes and are present in detectable amounts in prenatal fluids including urine, plasma, and serum, as well as in amniotic fluid. It has also surprisingly been found that meconium antigens have sufficient specificity in complex fluids including serum, urine, and amniotic fluid to be detected by chromatographic methods or to be recognized by anti-meconium antibodies without prior purification.

Antibodies of the present invention specifically bind meconium antigens. While a meconium antigen may also exist in other body tissues, to be useful in the present invention, the antigen must have sufficient specificity in the sample fluid to be recognized as diagnostic of meconium. For example, meconium contains colonic epithelium antigens which may also be present in adult colon. While an antibody to this antigen may recognize both meconium and colon tissue, antibody detection of this antigen in prenatal urine would be diagnostic of meconium in amniotic fluid.

In the preferred method of the invention, prenatal maternal fluid, such as prenatal urine, is collected one or more times during pregnancy, up to and including labor and rupture of the amniotic membranes, and analyzed for the presence of meconium. Amniotic fluid may likewise be tested when available during pregnancy and at rupture of the amniotic membranes for the presence of meconium by the claimed method invention, but this is not a preferred, routine analytical sample. Recognition of a meconium antigen in maternal fluids alerts the physician to more carefully monitor the pregnancy and delivery.

The invention may be further understood by reference to the following examples.

EXAMPLE 1

CORRELATION OF MECONIUM ANTIGENS AND MECONIUM STATE PREGNANCY

Urine samples were collected from women at time of labor, as well as from non-pregnant women and men, and analyzed for the presence of meconium as described below. At time of rupture of the amniotic membranes, the amniotic fluid was visually analyzed for meconium staining. Results from the urine analysis were correlated to results from amniotic fluid analysis.

Unfractionated urine samples were applied to 4–20% gradient SDS polyacrylamide gels. Thirty microliters of each urine sample was combined with 15 µl of sample buffer for application to the gel wells. A meconium control was prepared by solubilizing a 0.5–0.7 g sample of meconium in 12.5 ml 0.1M tris (hydroxymethyl) amniomethane, pH 7.0, containing 1% (W/V) sodium dodecyl sulfate overnight on a reciprocating shaker. After dialysis against phosphate buffered saline, pH 7.4, one ml of 1.5 mg/ml solution of meconium was diluted with 0.5 ml running buffer. A 30µl aliquot of this solution was added to the gel well. After separation, the gels were stained with Commassie blue and protein patterns were examined.

As shown in Table 1, a protein antigen of approximately 14 KD was present in the urine of sample 6, which patient demonstrated dark staining amniotic fluid at parturition. This 14 KD antigen was also present in sample 2, which patient demonstrated problems at delivery characteristic of the presence of meconium, despite only light meconium staining. In contrast, control, non-pregnant urine and control male urine did not present this 14 KD antigen. Of the two prenatal urine samples obtained from patients who presented clear amniotic fluid at delivery, one did not contain the 14 KD antigen (sample No. 4) and one did (sample No. 5). This data indicates the assay method of this invention can detect meconium in prenatal urine with greater sensitivity than gross inspection of amniotic fluid.

TABLE 1

| SAMPLE NO. | SAMPLE TYPE | DELIVERY DETAILS | 14 KD ANTIGEN |
|---|---|---|---|
| 1 | NON-PREGNANT FEMALE URINE | — | – |
| 2 | PRENATAL URINE | SEVERE PIH* LIGHT MECONIUM | + |
| 3 | PRENATAL URINE | LIGHT MECONIUM | – |
| 4 | PRENATAL URINE | CLEAR FLUID | – |
| 5 | PRENATAL URINE | CLEAR FLUID | + |
| 6 | PRENATAL URINE | DARK MECONIUM | + |
| 7 | MALE URINE | — | |
| 8 | MECONIUM CONTROL | — | + |

*PIH = pregnancy induced hypertension

EXAMPLE 2

PREPARATION OF ANTIBODIES TO MECONIUM

To prepare anti-meconium antibodies, approximately 50 mg of meconium was injected, either with (DMI) Freund's adjuvant or without (DMZ), into New Zealand rabbits at multiple sites. Pre-immunization serum samples were obtained and frozen. Post-immunization serum was obtained at six and 12 weeks.

Serum samples were tested for reactivity with meconium by Western Blot analysis. Control meconium was prepared and separated on electrophoretic gels as described for Example 1. Meconium proteins were transferred from the polyacrylamide matrix onto nitrocellulose. To accomplish the transfer, the polyacrylamide gel was pre-equilibrated in TRIS-Gly SDS-20% MeOH buffer for thirty minutes. The antigens were then transferred to 0.2 micron nitrocellulose at 180 mA for 20 minutes. After transfer, the nitrocellulose was blocked in BLOTTO overnight at 4° C.

Antibodies raised against meconium were screened for their ability to bind the nitrocellulose blot containing meconium antigens. Approximately one milliliter each antibody was mixed with 2 ml of human plasma at 37° C. for approximately four hours to block non-specific binding. Precipitated material was removed by centrifugation at 18,000×G for approximately 2 hours at 4° C. A volume of 1.5 ml of the resultant antibody mixture was combined in 25 ml BLOTTO, and incubated with the nitrocellulose blot overnight at 4° C. This first antibody solution was decanted from the blot; the blot washed four times with 30 ml buffer for 15 minutes each time, and second antibody applied. The second antibody was goat-anti-rabbit diluted 1/1000 (Biorad 170-6515 #72734) prepared as 35 µl in 35 ml buffer containing 5% BLOTTO. The nitrocellulose blot was incubated with second antibody for approximately two hours at 37° C. the washed four times with 30 ml buffer as described above, then two times with 30 ml H$_2$O immediately prior to the addition of color reagents.

A color reaction due to the presence of secondary antibody on the blot was developed by adding DAB substrate (using 25 mg/100 ml buffer). Two positive antisera DM1 and DM2 were selected for use in further studies of antibody binding to meconium.

EXAMPLE 3

DETECTION OF MECONIUM ANTIGENS IN PRENATAL PREGNANT URINE BY WESTERN BLOT ANALYSIS

Urine specimens were obtained from women during labor, analyzed, and correlated with visual inspection of amniotic fluid and delivery conditions as described for Example 1. The urine specimens were dialyzed in sodium bicarbonate, lyophilized and reconstituted to a final excess concentration of ten fold in 50 mM TRIS, pH 7.2. Thirty microliters of the concentrated urine samples were combined with 15 µl of gel buffer and applied to gel wells. Non-pregnant female control urine, control male urine, and control meconium were also analyzed. Control meconium was prepared as described for Example 1. Twenty microliters of the control meconium solution was applied to the gel.

The concentrated urine samples were separated on a 4-20% gradient gel as described for Example 1 the proteins were transferred to nitrocellulose as described for Example 2.

Antibodies raised against meconium as described in Example 2 were utilized to probe the nitrocellulose blot for meconium antigens. Approximately one milliliter each of antibodies DM1 and DM2 were mixed together with 2 ml of human plasma at 37° C. for approximately four hours to block non-specific binding. Precipitated material was removed by centrifugation at 18,000×G for approximately 2 hours at 4° C. A volume of 1.5 ml of the resultant antibody mixture was combined in 25 ml BLOTTO, and incubated with the nitrocellulose blot overnight at 4° C. This first antibody solution was decanted from the blot; the blot washed four times with 30 ml buffer for 15 minutes each time, and second antibody applied. The second antibody was goat-anti-rabbit diluted 1/1000 (Biorad 170-6515 #72734) prepared as 35 µl in 35 ml buffer containing 5% BLOTTO. The nitrocellulose blot was incubated with second antibody for approximately two hours at 37° C., then washed four times with 30 ml buffer as described above, then two times with 30 ml $H_2O$ immediately prior to the addition of color reagents.

Figure 2:
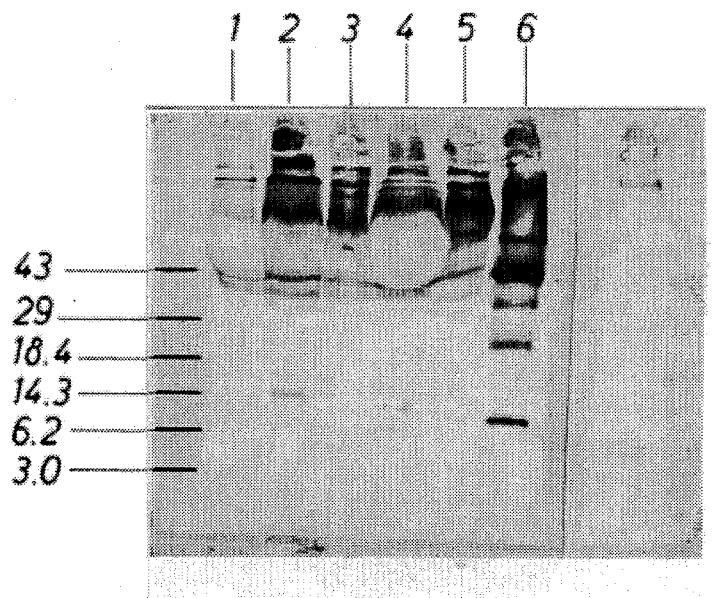
FIG. 2 is a photograph of a Western Blot showing test samples of Example 3 probed with an anti-meconium antibody.

As shown in Table 2, and FIG. 2, the anti-meconium antibodies bound to meconium antigens, including the 14 KD antigen, in the meconium control (sample 6) and in urine samples of patients presenting meconium in amniotic fluid at delivery (samples 2 and 4). The 14 KD antigen was not present in non-pregnant urine, male urine, nor in prenatal urine of a pregnancy which presented clear amniotic fluid at delivery with no meconium-associated conditions.

TABLE 2

| SAMPLE NO. | SAMPLE TYPE | DELIVERY DETAILS | 14 KD ANTIGEN |
|---|---|---|---|
| 1 | NON-PREGNANT FEMALE URINE | — | — |
| 2 | PRENATAL URINE | LIGHT MECONIUM STAINING | + |
| 3 | PRENATAL URINE | CLEAR AMNIOTIC FLUID | — |
| 4 | PRENATAL URINE | DARK MECONIUM STAINING | + |
| 5 | MALE URINE | — | — |
| 6 | MECONIUM CONTROL | — | + |

EXAMPLE 4

Prenatal urine samples were collected during labor and prepared by dialysis and lyophilization, and reconstituted to 10×concentration as described above for Example 3. Urine selected for analysis was that from patients who at delivery had clear amniotic fluid, lightly stained meconium amniotic fluid, and dark meconium staining. Male urine was used as a control. The concentrated urine samples were analyzed by PAGE on a 4-20% gradient gel as described for Example 1, and stained with Commassie blue. As shown in Table 3, the 14,000 molecular weight meconium antigen was not detected in the prenatal urine sample resulting in clear amniotic fluid at term, was faintly present in the urine sample resulting in light meconium staining at delivery, and was heavily present in the urine sample of the pregnancy which resulted in darkly stained meconium at term. Non-pregnant female urine and male urine did not contain this 14 KD antigen.

TABLE 3

| SAMPLE NO. | SAMPLE TYPE | DELIVERY DETAILS | 14 KD ANTIGEN |
|---|---|---|---|
| 1 | NON-PREGNANT FEMALE URINE | — | — |
| 2 | PRENATAL URINE | LIGHT STAINING | + |
| 3 | PRENATAL URINE | NONE | — |
| 4 | PRENATAL URINE | VERY DARK STAINING | + |
| 5 | MALE URINE | — | — |

EXAMPLE 5

MECONIUM ANTIGENS IN PRENATAL URINE

Prenatal urine obtained from patients during labor and correlated with visual inspection of amniotic fluid at delivery, was prepared and analyzed by polyacrylamide gel electrophoresis and Western blot analysis as described for Example 3. As shown in FIGS. 1 and 2, many specific meconium antigens were detected in the urine of women presenting stained amniotic fluid at delivery.

EXAMPLE 6

PREPARATION OF SPECIFIC ANTI-MECONIUM ANTIBODIES

To prepare specific anti-meconium antibodies a known meconium sample such as solubilized meconium or prenatal fluid obtained from a woman who presented meconium stained amniotic fluid or a specific meconium antigen such as those described in Example 5 is used to generate antibodies, e.g., by one or two dimensional gel electrophoresis, and used to generate anti-meconium antibodies. For example, specific meconium antigens are excised or eluted from electrophoretic gels or nitrocellulose blot and used with or without adjuvant as a vaccine to induce production in animals. The antigen may be purified or not. For example, a meconium sample may be separated by one or two dimensional gel electrophoresis, and specific meconium antigen excised and/or eluted for use in antibody production.

To produce polyclonal antibodies, meconium antigen is injected into rabbits and the resultant antisera screened for anti-meconium activity. To produce monoclonal antibodies, antigen meconium is used to inoculate mice, e.g., intraperitoneally, spleen cells are retrieved and fused with myeloma cells to form hybridomas. The hybridomas are screened for the production of specific anti-meconium antibodies. (Methods for producing monoclonal and polyclonal antibodies are described, for example, in Dunbar, BS, *Gel Electrophoresis and Immunological Techniques*, which is hereby incorporated by reference.)

Polyclonal antisera and monoclonal antibodies are screened for anti-meconium binding activity by incubating with meconium antigens. For example, electrophoretic gels, dot blots, or nitrocellulose transfers of control meconium, prenatal fluid from women having meconium stained amniotic fluid at delivery, and non-pregnant urine are incubated with antibodies. A marker system such as a dye-conjugated second antibody is then reacted with antibody-bound meconium samples. A positive signal indicates the presence of anti-meconium antibodies, which may be further analyzed, e.g., by Western blots to determine binding to specific meconium antigen.

EXAMPLE 7

PRENATAL SCREENING FOR MECONIUM

Urine or serum samples collected from pregnant women during routine prenatal examinations and preferably during the last trimester is analyzed for the presence of meconium antigens. The urine or serum may be concentrated or otherwise prepared for analysis. The sample is then analyzed by chromatographic methods, (e.g., polyacrylamide gel electrophoresis) for the presence of the 14 KD meconium antigen or another specific meconium antigen. Alternatively, the sample is analyzed by immunological methods (e.g., binding of specific anti-meconium antibodies in an ELISA or dot blot assay) or by a combination of chromatographic and immunological methods. Recognition of a meconium antigen in the urine or serum sample, or alternatively in an amniotic fluid sample is diagnostic of meconium stage pregnancy and alerts the physician to carefully monitor the delivery.

In the prenatal diagnostic test for meconium, a microliter test well, nitrocellulose paper, or other suitable assay surface is coated with or has bound thereto a specific meconium antigen capture reagent. This capture reagent is for example, an anti-meconium antibody, an antibody raised against the 14 KD meconium antigen, or antibody specific to another meconium antigen, as described for Example 6. The anti-meconium antibody is reacted with the test sample for a time and under conditions sufficient to permit binding any contained meconium antigen with the antibody.

A marker system, such as a dye or fluorescent-conjugated second antibody, is then reacted with the antibody-antigen complex to generate a signal which is correlated to the presence and/or amount of meconium in the test sample.

I claim:
1. A method for detecting prenatal meconium excretion by a fetus comprising the steps of:
   chromatographically separating proteins in a sample obtained from maternal prenatal fluid or amniotic fluid;
   analyzing the separated proteins for the presence of a meconium antigen of approximately 14 KD; and
   correlating the presence of the meconium antigen with excretion of meconium by the fetus.
2. The method of claim 1, wherein said sample is selected from the group consisting of maternal urine, maternal serum, and maternal plasma.
3. The method of claim 2 wherein said sample is maternal urine.
4. The method of claim 1, wherein said sample is amniotic fluid.
5. The method of claim 1, wherein said chromatographic separation is by polyacrylamide gel electrophoresis.
6. The method of claim 1, wherein said analyzing comprises reacting the separated proteins with an anti-meconium antibody, which antibody specifically binds the meconium antigen, whereby meconium antigen present in the sample forms antigen-antibody complexes with the anti-meconium antibody, and detecting said antigen-antibody complexes to indicate the presence of the meconium antigen.
7. A method for determining the presence of meconium in a test sample comprising the steps of:
   reacting a sample suspected of containing meconium with an anti-meconium antibody, which antibody specifically binds a meconium antigen of approximately 14 KD, whereby meconium antigen present in the sample forms an antigen-antibody complex with the anti-meconium antibody;
   detecting antibody-antigen complex with a marker system; and
   correlating the presence of the antigen-antibody complex with the presence of meconium in the sample.
8. A method for detecting prenatal meconium excretion by a fetus comprising:
   immobilizing proteins of a maternal prenatal fluid or amniotic fluid sample on a test surface;
   reacting said immobilized proteins with an anti-meconium antibody which antibody specifically binds a meconium antigen of approximately 14 KD to form an antigen-antibody complex;
   analyzing the test surface for the presence of antigen antibody complexes; and
   correlating the presence of antigen-antibody complexes with the excretion of meconium by the fetus.
9. An anti-meconium antibody which specifically binds a meconium antigen of approximately 14 KD.
10. A diagnostic kit useful in screening prenatal urine for the presence of meconium, the kit comprising:
   an anti-meconium antibody which antibody specifically binds a meconium antigen of approximately 14 KD to form an antigen-antibody complex; and
   a marker system for determining the presence of the antigen-antibody complex.

* * * * *